(12) United States Patent
Henry et al.

(10) Patent No.: US 8,815,305 B2
(45) Date of Patent: Aug. 26, 2014

(54) COMPOSITION CONTAINING A PLANT EXTRACT AND PROCESS FOR PRODUCING SAME

(75) Inventors: Florence Henry, Villers-les-Nancy (FR); Louis Danoux, Saulxures les Nancy (FR); Gilles Pauly, Nancy (FR); Zoubida Charrouf, Rabat R.P. (MA)

(73) Assignee: BASF Beauty Care Solutions France S.A.S., Lyons (FR)

( * ) Notice: Subject to any disclaimer, the term of this patent is extended or adjusted under 35 U.S.C. 154(b) by 439 days.

(21) Appl. No.: 10/576,816

(22) PCT Filed: Oct. 15, 2004

(86) PCT No.: PCT/EP2004/011625
§ 371 (c)(1),
(2), (4) Date: Apr. 24, 2006

(87) PCT Pub. No.: WO2005/039610
PCT Pub. Date: May 6, 2005

(65) Prior Publication Data
US 2007/0281047 A1    Dec. 6, 2007

(30) Foreign Application Priority Data
Oct. 24, 2003  (EP) ..................... 03292668

(51) Int. Cl.
*A61K 36/00*   (2006.01)

(52) U.S. Cl.
USPC ......................... 424/725; 424/777

(58) Field of Classification Search
None
See application file for complete search history.

(56) References Cited

U.S. PATENT DOCUMENTS

| | | | |
|---|---|---|---|
| 6,616,936 B1 * | 9/2003 | Martin et al. .................. | 424/401 |
| 2003/0138394 A1 * | 7/2003 | Charrouf et al. ................ | 424/74 |

FOREIGN PATENT DOCUMENTS

| | | | |
|---|---|---|---|
| DE | EP 1213025 A1 * | 6/2002 | |
| EP | 1213025 A1 * | 6/2002 | |
| EP | 1 430 900 | 6/2004 | |
| FR | 2692783 A1 * | 12/1993 | |
| FR | 2 723 316 | 2/1996 | |
| FR | 2724663 A1 * | 3/1996 | |
| JP | 05 186326 | 7/1993 | |
| WO | WO 01/82885 | 11/2001 | |
| WO | WO 02/45728 | 6/2002 | |
| WO | WO 02/45729 | 6/2002 | |
| WO | WO 02/055639 | 7/2002 | |

OTHER PUBLICATIONS

Charrouf et al., Triterpenes and sterols isolated from the pulp of *Argania spinosa* (L.), Sapotaceae, Plantes Medicinales et Phytotherapie 25 (2-3), 112-117, 1991.*

Chernane et al, Phenolic composition of the pulp of fruits of argan (*Argania spinosa*) in relation to morphological characteristics Composition phenolique de la pulpe des fruits d'arganier (*Argania spinosa* L. Skeels) et relation avec leurs caracteristiques morphologiques, Agrochimica, (1999) vol. 43, No. 3/4, pp. 137-150.*

Basu-Modak et al, Epicatechin and its methylated metabolite attenuate UVA-induced oxidative damage to human skin fibroblasts, Free radical biology & medicine, (Oct. 15, 2003) vol. 35, No. 8, pp. 910-921.*

Katiyar et al, Green tea polyphenolic antioxidants and skin photoprotection (review), International Journal of Oncology 18: 1307-1313, 2001.*

Wang et al, Extraction of tea polyphenol, Guangzhou Huagong (2001), 29(4), 27-29.*

Charrouf et al., "Triterpenes et Sterols Extraits de la Pulpe D'*Argania spinosa* (L) Sapotaceae", Plantes Medicinales et Phytotherapie, Angers, FR, vol. 25, 1991, pp. 112-117; XP000619575.

Charrouf et al., "Ethnoeconomical, Ethnomedical, and Phytochemical Study of *Argania spinosa* (L.) Skeels: A Review", Journal of Ethnopharmacology vol. 67, 1992, pp. 7-14; XP002242296.

Fellat-Zarrouck et al., "Etude de la pulpe du fruit de farganier (*Argania spinosa*) du Maroc. Matiere grasse et latex", Actes Inst. Agros. Vet., vol. 87, 1987, pp. 17-22.

Mitaine-Offer et al., "Triterpenes and Phytosterols as Human Leucocyte Elastase Inhibitors", Laboratoire de Pharmacognosie, Faculte de Pharmacie, Universite de Reims Champagne-Ardenne, Planta Med 2002, vol. 68, 2002, pp. 930-932.

Rajic et al., "Inhibition of Serine Proteases by Anti-Inflammatory Triterpenoids", Planta Medica 66, 2000, pp. 206-210.

Kweifio-Okai et al., "Antilipoxygenase activity of amyrin triterpenes", Research Communications in Chem. Pathology and Pharmacology, vol. 78, 1992, pp. 367-372.

Zitterl-Eglseer, et al., "Anti-oedematous activities of the main triterpendiol esters of marigold (*Calendula officinalis* L.)", Journ.of Ethno-Pharmacology, vol. 57, 1997, pp. 139-144.

Máñez et al., "Effect of selected triterpenoids on chronic dermal inflammation", European Journ.of Pharmacology, vol. 334, 1997, pp. 103-105.

Ying et al., "Inhibition of human leucocyte elastase by ursolic acid", Biochem J.. 1991, vol. 277, pp. 521-526.

Marion M. Bradford, "A Rapid and Sensitive Method for the Quantitation of Microgram Quantities of Protein Utilizing the Principle of Protein-Dye Binding", Analytical Biochemistry, 1976, vol. 72, pp. 248-254.

Hissin et al., "Fluorometric method for determination of oxidised and reduced Glutathione in tissues", Analytical Biochemistry, vol. 74, 1976, pp. 214-226.

(Continued)

*Primary Examiner* — Qiuwen Mi
(74) *Attorney, Agent, or Firm* — Servilla Whitney LLC

(57) ABSTRACT

A composition which includes a pulp extract from the fruit of *Argania spinosa* and at least one dermopharmaceutical or cosmetic auxiliary and/or additive is provided. A process for producing an extract from the fruit of *Argania spinosa*, and a triterpene fraction of an extract of the pulp of the fruit of *Argania spinosa* including lupeol, α-amyrine, β-amyrine, taraxasterol, and psi-taraxasterol are also provided.

12 Claims, No Drawings

(56) References Cited

OTHER PUBLICATIONS

Dalle Carbonare et al., "Skin photosensitizing agents and the role of reactive oxygen species in photoaging", J. Photochem.Photobiol., 1992, vol. 14, pp. 105-124.

Mortiere et al, "UVA-induced lipid peroxidation in cultured human fibroblasts", Biochimica et Biophysica Acta, 1991, 1084, pp. 261-269.

De Leo et al., "Ultraviolet radiation stimulates the release of arachidonic acid from mammalian cells in culture", Photochemistry and Photobiology, 1985, vol. 41, pp. 51-56.

Bonnekoh et al., "Lactate dehydrogenase release as an indicator of dithranol-induced membrane injury in cultured human keratinocytes", Arch Dermatol Res, 1990, vol. 282, pp. 325-331.

Kasprzyk et al., "Triterpenic Alcohols of *Calendula officinalis* L. Flowers," Phytochemistry, vol. 7, 1968, pp. 1631-1639.

Japanese Office Action.

Simone K. Yoda, et al.: Supercritical fluid extraction from *Stevia rebaudiana* Bertoni using CO2 and CO2 + water: extraction kinetics and identification of extracted components. In: Journal of Food Engineering 57 (2003) pp. 125-134.

Shang, Bing et al.: Effect of a amyrin extracted from *Cichorium intybus* on membrane microviscosity of rabbit aortic smooth muscle cells. Chemical Abstracts, AN 1999:449453.

M. Nagaraj, et al.: Effect of Lupeol, a Pentacyclic Triterpene, on the Lipid Peroxidation and Antioxidant Status in Rat Kidney after Chronic Cadmium Exposure. In: Journal of Applied Toxicology, Taxicol. 20, (2000), pp. 413-417.

G. Kweifio-Okai, et al.: Antiarthritic Mechanisms of Amyrin Triterpenes. In: Research Communications in Molecular Pathology and Pharmacology, vol. 85, No. 1, Jul. 1994, pp. 45-56.

Charrouf et al., "Triterpenes et Sterols Extraits de Ia Pulpe D'*Argania spinosa* (L) *Sapotaceae*", Plantes Medicinales et Phytotherapie, Angers, FR, vol. 25, 1991, pp. 112-117; XP000619575.

Charrouf et al., "Ethnoeconomical, Ethnomedical, and Phytochemical Study of *Argania spinosa* (L.) Skeels: A Review", Journal of Ethnopharmacology,, vol. 67, 1992, pp. 7-14; XP002242296.

Fellat-Zarrouck et al., "Etude de Ia pulpe du fruit de l'arganier (*Argania spinosa*) du Maroc. Matiere grasse et latex", Actes Inst. Agros. Vet., vol. 87, 1987, pp. 17-22.

Morliere et al., "UVA-induced lipid peroxidation in cultured human fibroblasts", Biochimica et Biophysica Acta, 1991, 1084, pp. 261-269.

* cited by examiner

COMPOSITION CONTAINING A PLANT EXTRACT AND PROCESS FOR PRODUCING SAME

RELATED APPLICATIONS

This national phase application is filed under 35 U.S.C. §371 from International Application No. PCT/EP2004/011625 filed Oct. 15, 2004, which designated the United States of America and which claims priority from European application EP 03292668.5 filed Oct. 24, 2003; the entire contents of each application are hereby incorporated herein by reference.

FIELD OF THE INVENTION

The present invention relates generally to an extract of the fruit of *Argania spinosa*, and more particularly to the compositions containing an extract of the pulp of the fruit of *Argania spinosa*, a process for obtaining same, and the incorporation of the extract in a medicament and a cosmetic preparation.

BACKGROUND INFORMATION

There is a rising demand for cosmetic preparations which have several properties simultaneously and thus exhibit an improved performance spectrum. Of particular interest are cosmetic preparations which have care properties and revitalizing properties and which protect against aging phenomena of the human skin or of human hair.

The active ingredients used in cosmetic preparations should contribute to (at least they should not deteriorate) important properties of the cosmetic preparations like storage stability, photostability and ability to be formulated easily. Good skin compatibility and the use of natural products is frequently requested by customers. Several plant extracts can serve this purpose. It is desirable, of course, to obtain significantly improved cosmetic preparations by combining active ingredients which are already known in the state of the art. Yet it can be a disadvantage to use a combination of active ingredients from extracts of different plants, because this increases the complexity of the product. Thus the production of the preparation can be more difficult and more expensive.

Extracts from plants and their ingredients are being used more and more frequently for cosmetic and for pharmaceutical purposes. In many cases the known effects of certain plant extracts are very specific and the field of use for these extracts is very limited.

The composition of many plant extracts is known. In these cases several individual chemicals have been identified in the plant extract. The properties of these chemicals are known in many cases. Nevertheless it is impossible to predict the properties of a plant extract from the information that certain chemical compounds with certain properties are contained in the extract. It remains the problem that a plant extract additionally contains unknown components in unknown quantities. These other components may in some cases overcompensate the effect that the known chemicals have. E.g. the information that a certain plant contains an antibiotic does not mean that its extract is useful for pharmaceutical purposes. It might well be the case that toxic substances in the extract render the extract itself completely useless for pharmaceutical applications. Whether a certain plant extract is useful for a certain purpose can only be decided after testing the extract itself with respect to the intended use.

It is known that specific parts of the plant *Argania spinosa* or the extracts thereof can be used for cosmetic purposes.

*Argania spinosa* means the plant that in detail is called *Argania spinosa* (L.) Skeels. "L." and "Skeels" denote the nomenclature system used.

*Argania spinosa* (belonging to the family of the Sapotaceae) is an endemic tree of Morocco. It grows on the west side of the Atlas mountains. The fruits of *Argania spinosa* have three parts: a pulp, a shell and oleaginous seeds. These three parts represent approximately 44%, 46% and 10% of the dry weight of the fruit. The pulp of the fruit of *Argania spinosa* can be used in dry or fresh form to feed cattle.

WO 01/82885 discloses a cosmetic and/or pharmaceutical preparation that contains saponins from an extract of the plant *Argania spinosa*.

WO 02/45729 discloses preparations containing native proteins from the plant *Argania spinosa* and the use of these proteins as skin care products and hair care products. These proteins can be obtained from the extract of the seeds of *Argania spinosa*.

WO02/45728 discloses a cosmetic and/or dermopharmaceutical preparation containing native proteins from the plant *Argania spinosa* as care agent for skin and hair.

European Patent Application, application number 02293130.7 (filed Dec. 18, 2002) discloses the use of extracts of *Argania spinosa* for various pharmaceutical purposes. Extracts containing saponins are used. Preferably the extract of the seeds is used.

There remains a need for extracts of plants for pharmaceutical and cosmetic applications.

SUMMARY OF THE INVENTION

In one embodiment, the invention includes a composition which includes a pulp extract from the fruit of *Argania spinosa* and at least one dermopharmaceutical auxiliary and/or additive. The pulp extract includes a non-saponifiable fraction of the pulp, and includes a triterpene-fraction of the pulp.

In another embodiment, the invention includes a composition which includes a component selected from the group of the pulp of the fruit of *Argania spinosa*, the non-saponifiable-fraction thereof, the triterpene-fraction thereof, lupeol, α-amyrine, β-amyrine, taraxasterol, and psi-taraxasterol and at least one cosmetic auxiliary and/or additive.

In another embodiment of the invention, a process for producing an extract from the fruit of *Argania spinosa* includes the steps of extracting the pulp from the fruit of *Argania spinosa* with a solvent selected from a hydrocarbon; a halogenated hydrocarbon; a $C_{1-6}$ alcohol; an ester of a $C_{1-6}$ carboxylic acid and a $C_{1-6}$ alcohol; a $C_{1-6}$ ketone; and a supercritical fluid to obtain a mixture comprising an extract and a solvent; and removing the solvent from the mixture. The process may include the further steps of saponifying the extract; separating the saponified extract substances from the non-saponifiable extract; and fractionating from the non-saponifiable extract the triterpene fraction which consists of lupeol, alpha-amyrine, beta-amyrine, taraxasterol and psi-taraxasterol.

In another embodiment of the invention, a triterpene fraction of an extract of the pulp of the fruit of *Argania spinosa* includes lupeol, α-amyrine, β-amyrine, taraxasterol, and psi-taraxasterol.

DETAILED DESCRIPTION OF THE INVENTION

The pulp of the fruit of *Argania spinosa* has been analysed. The results are disclosed in the thesis of Z. Charrouf (dated 1991): Fella-Zarrouk, K., Smoughen, S. and Maurin, R. (1987) "Etude da la pulpe de fruit de l'arganier du Maroc. Matiere grasse et latex. Actes Ins. Agro. Vet. Rabat 7, 17-22. Information can also be found in the review article "Ethno-economical, ethnomedical and phytochemical study of *Argania spinosa*", Journal of Ethnopharmacology, November 1998.

An analysis of the pulp of the fruit of *Argania spinosa* may typically reveal the following composition. 15 to 25% of moisture, 2 to 4% ashes, 29 to 53% glucosides (including 15 to 25% reducing sugars, 5 to 15% of non-reducing sugars, 9 to 3% of hemicellulose), 6 to 12% cellulose, 5 to 10% lipids, 6 to 8% nitrogen derivatives and 1% of polyphenols, mainly tannins.

A specific analysis of the pulp of the fruit of *Argania spinosa* may reveal the following composition. 20 to 50% of moisture, 4.1% of ashes, 12.9% of cellulose, 5.9% of nitrogen derivatives, 6% of lipids and 18% of glucosides.

The lipid fraction of the pulp of the fruit of *Argania spinosa* may typically contain 33.3% glycerides, 63% latex and 3.3% unsaponifiable substances. The unsaponifiable fraction contains triterpenoids and sterols.

Amongst the triterpenoids the following have been identified individually:

Lupeol, which is a lupane triterpene (CAS number: 545-47-1 MW: 426.724)

Synonyms for lupeol are: Monogynol B, Fagarasterol, Viscol, Cautchicol, Xanthosterin, Clerodol.

Lupeol is known to have the following biological activities. It is an antineoplastic, it is a chymotrypsin and trypsic inhibitor, it is a hepatoprotector, it acts anti-inflammatory, it is an elastase inhibitor (this has been tested with human leucocytes).

α-amyrine, which is an ursane type triterpene (CAS number: 638-95-9 MW: 426,73)

Synonyms for α-amyrine are: 12-Ursen-3-ol3β form, Amyrenol, Viminalol.

α-Amyrine is known to have the following biological activities. It is an antineoplastic, it is an hymotrypsin and trypsic inhibitor, it inhibits lipoxygenase.

β-amyrine, which is a oleanane type triterpene (CAS number: 559-70-6 MW: 426,73)

Synonyms for β-amyrine are: 12-Oleanen-3-ol3β form, Amyrenol, Viscol-Amirin.

β-Amyrine is known to have the following biological activities. It has anti-inflammatory properties, it is an elastase inhibitor (this has been tested with human leucocytes), and it inhibits lipoxygenase.

taraxasterol, which is an ursane type triterpene (CAS number: 1059-14-9 MW: 426,73)

Synonyms for taraxasterol are: 20(30)-Taraxasten-3-ol (3β,18α,19α)-form, Lactucero, -Anthesterin, Taraxasterin, Inusterol A, Pyrethrol, Saussurol.

Taraxasterol is known to have the following biological activities. It acts anti-inflammatory erythrodiol, which is an oleanane type triterpene (CAS number: 545-48-2 MW: 442,72)

Synonyms of erythrodiol are: 12-Oleanene-3,28-diol 3βform, Homoolestranol.

Erythrodiol is known to have the following biological activities. It acts anti-inflammatory, it is an elastase inhibitor (this has been tested with human leucocytes).

Amongst the sterols schottenol and spinasterol have been identified.

The latex of the lipid fraction contains cis-polyisoprene and trans-polyisoprene (typically 86% and 14% respectively).

The following references are useful in order to understand the background of the present invention. These references disclose the properties of triterpenes. Some of these triterpenes can be found in the extract of *Argania spinosa*. The references are presented in the form of abstracts that can be retrieved in common databases.

Triterpenes and phytosterols as human leucocyte elastase inhibitors.—Mitaine-Offer A C, Hornebeck W, Sauvain M, Zeches-Hanrot M.—Laboratoire de Pharmacognosie, Faculte de Pharmacie, Universite de Reims Champagne-Ardenne, Reims, France.—Planta Med. 2002 October; 68(10):930-2.—Ten triterpenes and phytosterols beta-amyrin, lupeol, lupeol acetate, ursolic acid, friedelin, canophyllol, 29-hydroxy-friedelan-3-one, beta-sitosterol, 3-O-beta-D-glucopyranosyl-beta-sitosterol, 3-O-(6'-O-palmitoyl)beta-D-glucopyranosyl-beta-sitosterol, were evaluated as potential inhibitors of human leucocyte elastase (HLE). In this series, lupeol, ursolic acid and canophyllol showed marked HLE inhibitory activity with IC(50) values at 1.9 microM, 4.4 microM, and 2.5 microM, respectively. It appeared that HLE inhibition depended on the presence and the orientation of two reactive groups in the tested molecules, distant from 10-12 A, reacting with Arg-217 in S(4)-S(5) subsites of the extended substrate-binding domain of HLE, and S(3), respectively.

Inhibition of serine proteases by anti-inflammatory triterpenoids.—Rajic A, Kweifio-Okai G, Macrides T, Sandeman R M, Chandler D S, Polya G M.—Planta Med. 2000 April; 66(3):206-10-Department of Biochemistry and Genetics, Bundoora, Victoria, Australia.—The lupane triterpenoid lupeol, the ursane triterpenoid alpha-amyrin and esters of these compounds are present in the bark of roots of *Alstonia boonei* (Apocynaceae) and have anti-inflammatory properties. alpha-Amyrin is a competitive inhibitor of bovine trypsin and chymotrypsin (Ki values 29 microM and 18 microM, respectively). Lupeol linoleate, lupeol palmitate and alpha-amyrin linoleate are non-competitive inhibitors of trypsin (Ki values 7 microM, 10 microM and 16 microM, respectively). alpha-Amyrin linoleate is also a non-competitive inhibitor of chymotrypsin (Ki value 28 microM). Lupeol is a competitive inhibitor of both trypsin and chymotrypsin (Ki values 22 and 8 microM, respectively). alpha-Amyrin palmitate is a potent non-competitive inhibitor of chymotrypsin (Ki 6 microM). Lupeol, alpha-amyrin and the palmitic and linoleic acid esters of these compounds are ineffective or very weak as inhibitors of porcine pancreatic elastase and of *Lucilia cuprina* and *Helicoverpa punctigera* leucine aminopeptidases. These hydrophobic triterpenoids represent further examples of anti-inflammatory triterpenoids that are PICA inhibitors as well as being selective protease inhibitors.

Antilipoxygenase activity of amyrin triterpene—Kweifio-Okai G, Macrides T A—Department of Anatomy and Physiology, Royal Melbourne Institute of Technology, Bundoora, Australia—Res Commun Chem Pathol Pharmacol. 1992 December; 78(3):367-72—Triterpenes—alpha-amyrin acetate, beta-amyrin acetate and beta-amyrin were tested for their effects on the synthesis of 5-lipoxygenase products in human neutrophils. All the triterpenes reduced 5-HETE synthesis without effect on LTB4 synthesis. The relative effects suggest that 5-HETE inhibition can explain the antiarthritic activity possessed by these compounds.

Anti-oedematous activities of the main triterpendiol esters of marigold (*Calendula officinalis* L.)—Zitterl-Eglseer K, Sosa S, Jurenitsch J, Schubert-Zsilavecz M, Della Loggia R, Tubaro A, Bertoldi M, Franz C—J Ethnopharmacol. 1997 July; 57(2):139-44-Institute for Botany and Food Science, University of Veterinary Medicine Vienna, Wien, Austria—Separation and isolation of the genuine faradiol esters (1,2) from flower heads of Marigold (Calendula (officinalis L., *Asteraceae*) could be achieved by means of repeated column chromatography (CC) and HPLC for the first time. Structure elucidation of faradiol-3-myristic acid ester 1, faradiol-3-palmitic acid ester 2 and psi-taraxasterol 3 has been also performed, without any previous degradation by means of MS, $^1$H-NMR, $^{13}$C-NMR and 2D-NMR experiments. The anti-oedematous activities of these three compounds were tested by means of inhibition of *Croton* oilinduced oedema of the mouse ear. Both faradiol esters showed nearly the same dose dependent anti-oedematous activity and no significant synergism appeared with their mixture. The free monol, psi-taraxasterol, had a slightly lower effect. Furthermore, faradiol was more active than its esters and than psi-taraxasterol and showed the same effect as an equimolar dose of indomethacin.

Effect of selected triterpenoids on chronic dermal inflammation—Manez S, Recio M C, Giner R M, Rios J L—Eur J. Pharmacol. 1997 Sep. 3; 334(1):103-5—Departament de Farmacologia, Universitat de Valencia, Spain—The activity of four natural triterpenoids on a 12-O-tetradecanoylphorbol-13-acetate multiple-dose model of skin chronic inflammation was studied. Erythrodiol and ursolic acid were significantly effective. The most important features concerning structure-activity relationship and previous data on the effect of these triterpenoids on other inflammatory conditions are discussed.

Inhibition of human leucocyte elastase by ursolic acid. Evidence for a binding site for pentacyclictriterpenes—Ying Q L, Rinehart A R, Simon S R, Cheronis J C—Biochem J. 1991 Jul. 15; 277 (Pt 2):521-6—Department of Pathology, State University of New York, Stony Brook 11794—Several pentacyclic triterpenoid metabolites of plant origin are inhibitors of hydrolysis of both synthetic peptide substrates and elastin by human leucocyte elastase (HLE). Ursolic acid, the most potent of these compounds, has an inhibition constant of 4-6 microM for hydrolysis of peptide substrates in phosphate-buffered saline. With tripeptide and tetrapeptide substrates, the inhibition is purely competitive, whereas with a shorter dipeptide substrate the inhibition is non-competitive, suggesting that ursolic acid interacts with subsite S3 of the extended substrate-binding domain in HLE, but not with subsites S1 and S2. The carboxy group at position 28 in the pentacyclic-ring system of the triterpenes contributes to binding to HLE, since replacement of this group with a hydroxy group, as in uvaol, the alcohol analogue of ursolic acid, reduces the potency of inhibition. The inhibitory potency of ursolic acid is also reduced by addition of 1M-NaCl, further supporting a postulated electrostatic interaction between the negative charge on the triterpene and a positively charged residue on the enzyme, which we assign to the side chain of Arg-217, located in the vicinity of subsites S4 and S5 in HLE. These observations are consistent with a binding site for ursolic acid which extends from S3 towards S4 and S5 on the enzyme. Other triterpenes, including oleanolic acid, erythrodiol, hederagenin and 18 beta-glycyrrhetic acid, can also interact with this binding site. On the basis of these results we conclude that the extended substrate-binding domain of HLE can accommodate a variety of hydrophobic ligands, including not only such molecules as fatty acids but also polycyclic molecules such as the pentacyclic triterpenoids.

The problem underlying the present invention is the need for substances that can be used in cosmetic applications. There is a need for such substances having a regenerating and revitalising effect on human skin and having a protective effect against UV-A and UV-B radiation.

Surprisingly it has been found that the extract of the pulp of the fruit of *Argania spinosa* as subsequently defined has several advantageous properties that render this extract useful for cosmetic applications. Amongst other properties the extract of the pulp of the fruit of *Argania spinosa* has a regenerating and revitalising effect on human fibroblasts and it has a protective effect against UV-A and UV-B radiation.

The use of the extract of the pulp of the fruit of *Argania spinosa* for cosmetic or pharmaceutical purposes is surprising and not obvious to the skilled artisan because to date the pulp of the fruit of *Argania spinosa* has been regarded and used only as a by-product of the fruit of low value. Up to now the oleaginous seeds have been used to produce oil for food or for cosmetic purposes. The pulp has been discarded or it has been used to feed cattle. The present invention provides for a use of the pulp of much higher value. Thus the use of the pulp for high value purposes like cosmetic and pharmaceutical applications means to recycle waste for high value applications.

The extract of the pulp of the fruit of *Argania spinosa* according to the present invention means the substances which are obtainable by extracting the pulp of the fruit of *Argania spinosa* with a solvent selected from the group consisting of hydrocarbons (preferably hexane or heptane), halogenated hydrocarbons, alcohols with 1 to 6 carbon atoms, esters of carboxylic acids with one to 6 carbon atoms and alcohols with 1 to 6 carbon atoms (preferably ethyl acetate), ketones with one to 6 carbon atoms (preferably acetone) and supercritical fluids (preferably supercritical carbon dioxide).

Preferred solvents are hexane and supercritical carbon dioxide, hexane is especially preferred.

The extract obtained by extracting the pulp of the fruit of *Argania spinosa* with hexane is lipophilic.

The extract obtained by extracting the pulp of the fruit of *Argania spinosa* with supercritical carbon dioxide is lipophilic.

The extract according to the present invention is obtainable by extracting of the pulp of the fruit of *Argania spinosa* with a solvent as previously defined to obtain a mixture comprising the extract and the solvent and by subsequently removing the solvent from the mixture thus obtained. Removing the solvent from the mixture can be done by distilling of the solvent or by other conventional methods.

In a specific embodiment of the present invention the extract of the pulp of the fruit of *Argania spinosa* is dried. The drying can be done before or after removing the solvent.

The extract of the pulp of the fruit of *Argania spinosa* is one subject of the present invention.

The extract of the pulp of the fruit of *Argania spinosa* contains a non-saponifiable-fraction. This non-saponifiable-fraction of the extract of the pulp of the fruit of *Argania spinosa* is another subject of the present invention.

The non-saponifiable-fraction is obtainable from the extract of the fruit of *Argania spinosa* by saponifying the extract according to known methods, preferably according to the IUPAC norm number 2.2401, and by subsequently removing the saponified substances and the substances that have been used to carry out the saponification.

The non-saponifiable-fraction of the extract of the pulp of the fruit of *Argania spinosa* contains a triterpene-fraction. The triterpene-fraction of the extract of the pulp of the fruit of *Argania spinosa* is another subject of the present invention.

The triterpene-fraction is obtainable from the non-saponifiable-fraction by chromatography. E. g. the unsaponifiable extract can be applied on the head of a chromatographic silica gel column, which is eluted with a hexane/ethyl acetate mixture to obtain a fraction that contains lupeol, α-amyrine, β-amyrine, taraxasterol and psi-taraxasterol and other substances. According to the present invention the fraction containing the substances listed in the previous sentence is called the triterpene-fraction.

The chromatography mentioned in the previous paragraph can be carried out on a silica gel column. It can also be carried out on polymethacrylate as adsorbent or on other conventional polymeric adsorbents or on reversed phase C-18 chromatography adsorbents. It may be carried out with a wide variety of solvents, e.g. with a hexane/ethyl acetate mixture or with supercritical fluids (preferably supercritical carbon dioxide or a mixture of carbon dioxide and methanol or ethanol or propanol in a supercritical state; supercritical carbon dioxide is the most preferred supercritical fluid).

The extract of the pulp of the fruit of *Argania spinosa* necessarily contains the non-saponifiable fraction of the extract of the pulp of the fruit of *Argania spinosa*. Thus the extract can be regarded to be a composition comprising the non-saponifiable fraction of the extract of the pulp of the fruit and further substances.

The non-saponifiable fraction of the extract of the pulp of the fruit of *Argania spinosa* necessarily contains the triterpene-fraction of the extract of the pulp of the fruit of *Argania spinosa*. Thus this non-saponifiable fraction can be regarded to be a composition comprising the triterpene-fraction of the extract of the pulp of the fruit of *Argania spinosa* and further substances. The further substances as defined in this paragraph can be different from the further substances as defined in the previous paragraph.

Another subject of the present invention is a substance selected from the group consisting of the triterpene-fraction according to claim 1, the non-saponifiable-fraction according to claim 2, the extract according to claim 3 and a composition comprising a) the triterpene-fraction according to claim 1 or the non-saponifiable-fraction according to claim 2 or the extract according to claim 3 and b) auxiliaries and/or additives which are common for pharmaceutical purposes for treatment of the human or animal body by therapy or diagnostic methods practised on the human or animal body.

Another subject of the present invention is the use of a substance selected from the group consisting of the triterpene-fraction according to claim 1, the non-saponifiable-fraction according to claim 2, the extract according to claim 3 and a composition comprising a) the triterpene-fraction according to claim 1 or the non-saponifiable-fraction according to claim 2 or the extract according to claim 3 and b) auxiliaries and/or additives which are common for pharmaceutical purposes for the manufacture of a medicament for the treatment of human skin that has been damaged by UV-A radiation or by UV-B radiation.

Another subject of the present invention is a composition comprising a) an ingredient selected from the group consisting of the triterpene-fraction according to the present invention, the non-saponifiable-fraction according to the present invention, the extract according to the present invention, lupeol, α-amyrine, β-amyrine, taraxasterol and psi-taraxasterol and b) auxiliaries and/or additives which are common for cosmetic purposes.

The auxiliaries and additives which are common for cosmetic purposes can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the auxiliaries and additives which are common for cosmetic purposes are selected from the group consisting of surfactants, emulsifiers, fats, waxes, stabilizers, deodorants, antiperspirants, antidandruff agents and perfume oils.

The composition in which the ingredient is selected from the group consisting of the triterpene-fraction according to the present invention, the non-saponifiable-fraction according to the present invention and the extract according to the present invention is preferred. Even more preferred is the composition in which the ingredient is the extract according to the present invention.

Another subject of the present invention is a process for the production of the extract according to the present invention comprising a) extracting of the pulp of the fruit of *Argania spinosa* with a solvent selected from the group consisting of hydrocarbons (preferably hexane or heptane), halogenated hydrocarbons, alcohols with 1 to 6 carbon atoms, esters of carboxylic acids with one to 6 carbon atoms and alcohols with 1 to 6 carbon atoms (preferably ethyl acetate), ketones with one to 6 carbon atoms (preferably acetone) and supercritical fluids (preferably supercritical carbon dioxide) to obtain a mixture comprising the extract and the solvent and b) removing the solvent from the mixture thus obtained.

Another subject of the present invention is the use of the triterpene-fraction according to the present invention or of the non-saponifiable-fraction according to the present invention or of the extract according to the present invention or of lupeol or of α-amyrine or of β-amyrine or of taraxasterol or of psi-taraxasterol or of the composition according to the present invention for the production of a cosmetic preparation.

Another subject of the present invention is the use of the triterpene-fraction according to the present invention or of the non-saponifiable-fraction according to the present invention or of the extract according to the present invention or of lupeol or of α-amyrine or of β-amyrine or of taraxasterol or of psi-taraxasterol or of the composition according to the present invention or of the cosmetic preparation according to the present invention for the cosmetic treatment of the human body.

One embodiment of the present invention is the use of the triterpene-fraction according to the present invention or of the non-saponifiable-fraction according to the present invention or of the extract according to the present invention or of lupeol or of α-amyrine or of β13-amyrine or of taraxasterol or of psi-taraxasterol or of the composition according to the present invention or of the cosmetic preparation according to the present invention for stimulating the metabolism of human skin, preferably the skin of male humans.

In the cases in which the subject of the present invention comprises a use as defined in the previous paragraphs it is preferred to use the triterpene-fraction according to the present invention or the non-saponifiable-fraction according to the present invention or the extract according to the present invention. It is even more preferred to use the extract according to the present invention.

The triterpene-fraction according to the present invention, the non-saponifiable-fraction according to the present invention and the extract according to the present invention have several advantageous properties. They can be used for cosmetic applications. They have a regenerating and revitalising effect on human fibroblasts and they have a protective effect against UV-A and UV-B radiation.

The compositions according to the present invention have good care and protecting properties for skin and hair, and also have high skin compatibility. They also exhibit a preventative and healing effect in cases of aging phenomena of the skin. They influence melanogenesis and exhibit an antiinflammatory and antimicrobial activity.

Furthermore they have a stimulating effect on the skin metabolism. Thus they help to clarify and to tone up the human skin. In particular they are useful for the improvement of the skin of male humans.

Furthermore they have a positive effect when used in the treatment of aged skin. They can help to fight against wrinkle appraising. They help to improve the renewal of cells and proteins in aged skin and thus they help to rejuvenate aged human skin.

Furthermore they can improve hair growth.

Furthermore they support the potential of human cells to fight against stress such as stress resulting from the exposure to pollutants or oxidative stress.

Furthermore they can be used as appeasing products to reduce inflammatory processes and to treat sensitive and/or acne's skin.

Furthermore they can be used to treat skin inflammation. In particular they can be used for the treatment of telangectiasy or "couperosis".

Furthermore they can be used to stimulate the synthesis of dermal macromolecules. In particular the synthesis of dermal macromolecules like glycosaminoglycans (such as hyaluronic acid, chondroitin-sulfate, dermatansulfat, keratansulfate) or like proteoglycans collagen and elastine can be stimulated.

Furthermore they can be used as active anti-aging ingredients because they can protect the DEJ by modulating some of its components. DEJ is the dermal-epidermal junction, DEJ is a specific structure lined the basal layer of epidermis and is formed from the organization of macromolecules such as Collagene type IV, Laminin, etc. The DEJ ensures the epidermis attachment to the dermis and control the exchange of nutriments and mediators between dermis and epidermis compartments.

Because of these numerous advantageous properties of the triterpene-fraction according to the present invention and of the non-saponifiable-fraction according to the present invention and of the extract according to the present invention the following subjects are further embodiments of the present invention.

A further embodiment of the present invention is the use of the triterpene-fraction according to the present invention or of the non-saponifiable-fraction according to the present invention or of the extract according to the present invention or of lupeol or of α-amyrine or of β-amyrine or of taraxasterol or of psi-taraxasterol or of the composition according to the present invention or of the cosmetic preparation according to the present invention for the treatment of aged human skin in order to fight against wrinkles.

A further embodiment of the present invention is the use of said substances for improving hair growth.

A further embodiment of the present invention is the use of said substances for improving the renewal of cells and of proteins in aged human skin and therefore to rejuvenate aged human skin.

A further embodiment of the present invention is the use of said substances for protecting human skin cells against UV and/or IR radiation.

A further embodiment of the present invention is the use of said substances for improving the potential of human cells to fight against stress like stress resulting from the exposure to pollutants or oxidative stress.

A further embodiment of the present invention is the use of said substances for reducing inflammatory processes.

A further embodiment of the present invention is the use of said substances for the treatment of sensitive skin and/or acne's skin.

A further embodiment of the present invention is the use of said substances for the treatment of telangectiasy or "couperosis".

A further embodiment of the present invention is the use of said substances for stimulating the synthesis of dermal macromolecules, e.g. glycosaminoglycans (such as hyaluronic acid, chondroitin-sulfate, dermatansulfat or keratansulfate), proteoglycans, collagen or elastine.

A further embodiment of the present invention is the use of said substances as active anti-aging ingredients based on their protective effect on the DEJ by modulating some of its components.

In all the embodiments defined in the previous paragraphs it is preferred to use the triterpene-fraction according to the present invention or the non-saponifiable-fraction according to the present invention or the extract according to the present invention. It is even more preferred to use the extract according to the present invention.

The extract, the unsaponifiable fraction or the triterpene fraction can be used in encapsulated form for cosmetic applications. Encapsulated form means that the active substance is encapsulated in liposomes or cyclodextrins or microparticles or otherwise.

Cosmetic treatment of the human body according to the present invention comprises the treatment of skin and/or hairs and/or skin appendices. Skin appendices means nails, sebaceous glands, sweat glands etc.

The extracts to be used according to the invention are prepared by customary methods of extraction. With regard to the suitable conventional extraction methods, such as maceration, remaceration, digestion, agitation maceration, fluidized-bed extraction, ultrasound extraction, countercurrent extraction, percolation, repercolation, evacolation (extraction under reduced pressure), diacolation and solid-liquid extraction under continuous reflux which is carried out in a Soxhlet extractor, each of which is known to the person skilled in the art. Starting material which may be used is fresh of dried pulp of the fruit, which can be mechanically reduced to small pieces prior to extraction. In this connection, all methods known to the person skilled in the art are suitable, mention being made by way of example to using a device containing blades.

The extraction usually takes place at 20 to 100° C., preferably at 80 to 100° C., in particular at the boiling temperature of the solvents or solvent mixtures. In one possible embodiment, the extraction is carried out under an inert gas atmosphere to avoid oxidation of the ingredients of the extract. The extraction times are adjusted by the person skilled in the art depending on the starting material, the extraction method, the extraction temperature, the ratio of solvent to raw material, etc. After the extraction, the resulting crude extracts can optionally be subjected to further customary steps, for example purification, concentration and/or decoloration. If desired, the extracts prepared in this way can, for example, be subjected to selective removal of individual undesired ingredients. The extraction can be carried out to any desired degree of extraction, but is usually carried out exhaustively.

The present invention encompasses the finding that the extraction conditions and also the yields of the end extracts can be chosen depending on the desired field of use.

The amount of plant extracts used in the compositions or cosmetic preparations according to the present invention is governed by the concentration of the individual ingredients and by the type of applications of the extracts. The total amount of the plant extract which is present in the preparations according to the invention is usually 0.01 to 25% by weight, preferably 0.03 to 5% by weight, in particular 0.03 to 0.6% by weight, calculated as dry weight, based on the compositions or preparations, with the proviso that the quantitative amounts add up to 100% by weight with water and optionally further auxiliaries and additives.

The total content of auxiliaries and additives may be 1 to 50% by weight, preferably 5 to 40% by weight, based on the cosmetic and/or dermopharmaceutical preparations. The preparations can be prepared by customary cold or hot processes; preference is given to using the phase-inversion temperature method.

For the purposes of the invention, active substance refers to the proportion of substances and also auxiliaries and additives which are present in the composition, with the exception of the additionally added water.

For the purposes of the invention, cosmetic preparations can mean care agents. Care agents are understood as meaning care agents for skin and hair. These care agents include, inter alia, cleansing and restorative action for skin and hair.

Application can be topical or orally in the form of tablets, dragees, capsules, juices, solutions and granules.

The compositions and cosmetic preparations according to the invention moreover exhibit an excellent skincare action coupled with simultaneously high skin compatibility. In addition, they exhibit good stability, in particular toward oxidative decomposition of the products. The preparations have a large number of cosmetic and dermopharmaceutical effects. The invention therefore further provides for the use of extracts from the pulp of the fruit of *Argania spinosa* as sunscreens, in particular against UVA radiation and/or against UVB radiation, as antioxidants, as antiinflammatory agents, as antimicrobial agents, as agents against skin aging, as protease-inhibiting agent except matrix metalloproteases (MMP), in particular as elastase-inhibiting agent and preferably as plasmin inhibitors and as pigmentation agents.

For the purposes of the invention, sunscreens or UV light protection factors are the terms used for light protection agents which are useful for protecting the human skin against harmful influences of direct and indirect solar radiation. The ultraviolet radiation from the sun which is responsible for tanning the skin is divided into the sections UV-C (wavelengths 200-280 nm), UV-B (280-315 nm) and UV-A (315-400 nm).

The pigmentation of normal skin under the influence of solar radiation, i.e. the form ation of melanins, is brought about by UV-B and UV-A in different ways. Irradiation with UV-A rays ("long-wave UV") results in the darkening of the melanin bodies already present in the epidermis, without harmful influences being evident. This is different in the case of so-called "short-wave UV" (UV-B). This brings about the formation of so-called delayed pigment as a result of the new formation of melanin granules. However, before the (protecting) pigment is formed, the skin is subject to the effect of unfiltered radiation which, depending on the exposure time, can lead to the formation of skin redness (erythema), skin inflammations (sunburn) and even blisters.

The UV absorbers or light filters, which thus convert the UV radiation into harmless heat, can be extracts from the pulp of the fruit of the plant *Argania spinosa*, these can additionally be present in combination with further sunscreens or UV light protection factors.

These further UV light protection factors are, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methylbenzylidene)camphor;

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, for example 2, 4,6-trianilino(p-carbo-2'-ethyl-1'-hexyloxy)-1,3,5-triazine and octyltriazone or dioctylbutamidotriazone (Uvasorb® HEB);

propane-1,3-diones, for example 1-(4-tert-butylphenyl)-3-(4'-methoxyphenyl)propane-1,3-dione;

ketotricyclo(5.2.1.0)decane derivatives

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzo-phenone-5-sulfonic acid and its salts;

sulfonic acid derivatives of 3-benzylidenecamphor, for example 4-(2-oxo-3-bornylidenemethyl)benzenesulfonic acid and 2-methyl-5-(2-oxo-3-bornylidene)sulfonic acid and salts thereof.

Suitable typical UV-A filters are, in particular, derivatives of benzoylmethane, for example 1-(4'-tert-butylphenyl)-3-(4'-methoxyphenyl)propane-1,3-dione, 4-tert-butyl-4'-methoxydi-benzoyl-methane (Parsol 1789), 1-phenyl-3-(4'-isopropylphenyl)propane-1,3-dione, and enamine compounds. The UV-A and UV-B filters can of course also be used in mixtures. As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skincare and skin-protective emulsions. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, for example titanium dioxide T 805 (Degussa) or Eusolex® T2000 (Merck). Suitable hydrophobic coating agents are here primarily silicones and, specifically in this case, trialkoxyoctylsilanes or dimethicones. In sunscreens, preference is given to using microor nanopigments. Preference is given to using micronized zinc oxide.

The extracts from the pulp of the fruit of the plant *Argania spinosa* are effective, for the purposes of the invention, against the damage to fibroblasts and/or keratinocytes by UV-A radiation and/or UV-B radiation.

UV-A rays penetrate into the dermis, where they lead to oxidative stress, which is demonstrated by a lipoperoxidation of the cytoplasma membranes. The lipoperoxides are degraded to malonaldialdehyde (MDA), which will crosslink many biological molecules such as proteins and nucleic bases (enzyme inhibition or mutagenesis). The extracts of the pulp of the fruit of *Argania spinosa* according to the invention significantly reduce the degree of MDA in human fibroblasts which is induced by UVA rays and thus exhibit a high capacity for reducing harmful effects of oxidative stress on the skin.

UVB rays trigger inflammation through activation of an enzyme, namely phospholipase A2 or PLA2. This inflammation (erythema, edema) is triggered by the removal of arachidonic acid from the phospholipids in the plasma membrane by the phospholipase. Arachidonic acid is the precursor of prostaglandins, which cause inflammation and cell membrane damage; the prostaglandins E2 PGE2) are formed by cyclooxygenase. The degree of release of the cytoplasm enzyme LDH (lactate dehydrogenase) in human keratinocytes serves as a marker for cell damage.

The extracts from the pulp of the fruit of the plant *Argania spinosa* according to the invention reduce the effect of UVB radiation on the number of keratinocytes and on the content of released LDH. Accordingly, the extracts have the ability to reduce the damage to cell membranes caused by UVB radiation.

For the purposes of the invention, the extracts from the pulp of the fruit of the plant *Argania spinosa* can act as an antioxidant or free-radical scavenger.

Antioxidants are able to inhibit or prevent the undesired changes in the substances to be protected caused by oxygen effects and other oxidative processes. The effect of the antioxidants consists in most cases in them acting as free-radical scavengers for the free radicals which arise during autoxidation.

As well as the use of extracts of the pulp of the fruit of *Argania spinosa* as antioxidants, further, already known antioxidants can also be used. A possible use of the antioxidants for example in cosmetic and/or dermopharmaceutical preparations is the use as secondary light protection agents, since antioxidants are able to interrupt the photochemical reaction chain which is triggered when UV radiation penetrates the skin. As well as the plant extract according to the invention, further typical examples thereof are amino acids (e.g. glycine, alanine, arginine, serine, threonine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene, lutein) or derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, boldin, boldo extract, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The further UV light protection factors or antioxidants can be added in amounts of from 0.01 to 25% by weight, preferably 0.03 to 10% by weight and in particular 0.1 to 5% by weight, based on the total amount in the compositions or cosmetic preparations according to the present invention.

The extracts from the pulp of the fruit of the plant *Argania spinosa* are effective, for the purposes of the invention, as antiinflammatory care agent which can heal inflammation of the skin or which can prevent inflammation. The inflammations here can have a very wide variety of causes. In particular, it is possible to treat inflammations which are induced by UV radiation, skin contaminations or bacterially or hormonally caused changes in the skin, e.g. acne.

The extracts from the pulp of the fruit of the plant *Argania spinosa* are effective, for the purposes of the invention, as antimicrobial agents, in particular against every type of bacterially caused skin change. This type of skin change includes infection by bacteria of a very wide variety of types and genera, for example staphylococci, streptococci, streptomycetes and/or propione bacteria.

The extracts from the pulp of the fruit of the plant *Argania spinosa* are effective, for the purposes of the invention, against skin aging, in particular against every type of wrinkling and line formation. Another name for this type of care agent is also anti-aging agent. The uses include a slowing of the aging processes of the skin. The aging phenomena can have a very wide variety of causes. In particular, these aging phenomena can be caused on the basis of apoptosis, damage to the skin induced by UV radiation or by the destruction of proteins endogenous to the skin, such as collagen or elastin.

The extracts according to the invention from extracts from the pulp of the fruit of the plant *Argania spinosa* act as protease-inhibiting agent except MMP, in particular as elastase-inhibiting agent and preferably as plasmin inhibitors. These proteases catalyze the fragmentation and destruction of the dermal macromolecules, such as proteoglycan, collagen and elastin, and thereby lead to aging of the skin and to the effects of natural skin aging following UV radiation.

As well as the already mentioned effects of the extracts from the pulp of the fruit of the plant *Argania spinosa*, positive effects were found in the influencing of melanogenesis. Melanogenesis refers to the natural synthesis of melanin in the cells, specifically the melanocytes. This natural pigmenting can be influenced by intervening in the reaction chain of the oxidation of tyrosine via L-DOPA to give melanin. Skin-lightening effects are achieved by inhibiting melanogenesis, whereas stimulation of melanogenesis may lead to increased pigmentation. The extracts from the pulp of the fruit of the plant *Argania spinosa*, exhibit stimulation of melanogenesis. These effects permit the use as pigmenting agent or as self-tanning agent.

As well as the various extracts from the pulp of the fruit of the plant *Argania spinosa*, the preparations can comprise further self-tanning agents or tyrosinase inhibitors. A suitable self-tanning agent is dihydroxyacetone. Suitable tyrosinase inhibitors, which prevent the formation of melanin and are used in depigmentation agents, are, for example, arbutin, ferulic acid, kojic acid, cumaric acid and ascorbic acid (vitamin C).

The use of the extracts according to the invention as protective and restorative care agents is in principle possible for all preparations which are used for prevention against damage or in the case of damage to the skin and/or the hair and thus in skincare and haircare. Another use in this field is the application in cases of sensitive skin damaged by allergy or other causes. The damage to the skin can have a very wide variety of causes.

The compositions and cosmetic preparations according to the invention can be used for the preparation of cosmetic and/or dermopharmaceutical preparations, e.g. hair shampoos, hair lotions, foam baths, shower baths, creams, gels, lotions, alcoholic and aqueous/alcoholic solutions, emulsions, wax/fat compositions, stick preparations, powders or ointments. Furthermore, the preparations for oral application according to the invention can also be incorporated into tablets, dragees, capsules, juices, solutions and granules.

These preparations can also comprise, as further auxiliaries and additives which are common for cosmetic purposes, oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, antidandruff agents, film formers, swelling agents, insect repellents, hydrotropes, solubilizers, preservatives, perfume oils, dyes and other auxiliaries and additives which are common for cosmetic purposes.

Surfactants (or Surface-active substances) which may be present are anionic, nonionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride(ether) sulfates, fatty acid amide(ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulfates, protein fatty acid condensates (in particular wheat-based vegetable products) and alkyl(ether) phosphates. If the anionic surfactants contain polyglycol ether chains, these may have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution. Typical examples of cationic surfactants are quaternary ammonium compounds, e.g. dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are exclusively known compounds. With regard to structure and preparation of these substances, reference may be made to relevant review works.

Typical examples of particularly suitable mild, i.e. particularly skin-compatible surfactants are fatty alcohol polyglycol ether sulfates, monoglyceride sulfates, monoand/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fattyacids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:
addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;
alkyl and/or alkenyl oligoglycosides having 8 to 22 carbon atoms in the alk(en)yl radical and the ethoxylated analogs thereof;
addition products of from 1 to 15 mol of ethylene oxide onto castor oil and/or hydrogenated castor oil;
addition products of from 15 to 60 mol of ethylene oxide onto castor oil and/or hydrogenated castor oil;
partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;
partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;
mixed esters of pentaerythritol, fatty acids, citric acid and fatty alcohols and/or mixed esters of fatty acids having 6 to 22 carbon atoms, methylglucose and polyols, preferably glycerol or polyglycerol,
mono-, di- and trialkyl phosphates, and mono-, di- and/or tri-PEG alkyl phosphates and salts thereof;
wool wax alcohols;
polysiloxane-polyalkyl-polyether copolymers and corresponding derivatives;
block copolymers, e.g. polyethylene glycol-30 dipolyhydroxystearates;
polymer emulsifiers, e.g. Pemulen grades (TR-1, TR-2) from Goodrich;
polyalkylene glycols, and
glycerol carbonate.

The addition products of ethylene oxide and/or of propylene oxide onto fatty alcohols, fatty acids, alkylphenols or onto castor oil are known, commercially available products. These are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known as refatting agents for cosmetic preparations.

Alkyl and/or alkenyl oligoglycosides, their preparation and their use are known from the prior art. They are prepared, in particular, by reacting glucose or oligosaccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera BeHine), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds which carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name *Cocamidopropyl Betaine*. Likewise suitable emulsifiers are ampholytic surfactants. The term "ampholytic surfactants" means those surface-active compounds which, apart from a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, Nhydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacylaminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also [lacuna] as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homolog distribution or alkyl oligoglucosides, and electrolytes such as sodium chloride and ammonium chloride.

Superfatting agents which can be used are substances for example lanolin and lecithin, and polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminum and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, for example Luviquat® (BASF), condensation products of polyglycols and amines, quaternized collagen polypeptides, for example lauryldimonium hydroxypropyl hydrolyzed collagen (Lamequat®L/Grünau), quatemized wheat polypeptides, polyethyleneimine, cationic silicone polymers, for example amodimethicones, copolymers of adipic acid and dimethylaminohydroxypropyldiethylenetriamine (Cartaretins®/Sandoz), copolymers of acrylic acid with dimethyldiallylammonium chloride (Merquat® 550/Chemviron), polyaminopolyamides and crosslinked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenyl-polysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Biogenic active ingredients that can be used are described in the following text. Within the scope of the invention, biogenic active ingredients are additionally understood as meaning those which do not arise from the plant *Argania spinosa*, for example tocopherol acetate, tocopherol palmitate, ascorbic acid, (deoxy)ribonucleic acid and fragmentation products thereof, retinol, bisabolol, allantoin, phytantriol, panthenol, AHA acids, amino acids, ceramides, pseudoceramides, essential oils, further plant extracts and additional vitamin complexes.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methyl-enebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or *styrax* or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexyl-propionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:

glycerol;
alkylene glycols, for example, ethylene glycol, diethylene glycol, propylene glycol, butylene glycol, hexylene glycol, and polyethylene glycols with an average molecular weight of from 100 to 1 000 daltons;
technical-grade oligoglycerol mixtures with a degree of self-condensation of from 1.5 to 10, for example, technical-grade diglycerol mixtures with a diglycerol content of from 40 to 50% by weight;
methylol compounds, such as trimethylolethane, trimethylolpropane, trimethylol-butane, pentaerythritol and dipentaerythritol;
lower alkyl glucosides, in particular those with 1 to 8 carbon atoms in the alkyl radical, for example methyl and butyl glucoside;
sugar alcohols with 5 to 12 carbon atoms, for example sorbitol or mannitol,
sugars with 5 to 12 carbon atoms, for example glucose or sucrose;
amino sugars, for example glucamine;
dialcohol amines, such as diethanolamine or 2-amino-1,3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, *costus*, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes. These dyes are normally used in concentrations of from 0.001 to 0.1% by weight, based on the total mixture.

EXAMPLES

Preparation of the Unsaponifiable Extract and of the Triterpene Fraction Used in the Experiments The triterpene fraction used in the experiments was prepared from a crude hexaneextract from crushed dry pulp of the fruit of *Argania spinosa*. This lipophilic extract was saponified according to the IUPAC norm number 2.401. The unsaponifiable extract was applied on the head of a chromatography column (silica gel) and eluted with a hexane/ethyl acetate mixture (a gradient was used, the ratio of hexane to ethyl acetete was not constant)

Three fractions were obtained by this elution:

Fraction A: containing active triterpenes, e.g. lupeol (approximately 50% by weight of fraction A), α-Amyrine (approximately 14% by weight of fraction A), β-amyrine (approximately 23% by weight of fraction A), taraxasterol and psi-taraxasterol.

Fraction B: containing delta 7 sterols, e.g. schottenol and spinasterol, and triterpenes and butinaldehyde Fraction C: consisting of the pure triterpene erythrodiol Fraction A was used as the triterpene fraction in the following experiments.

The following yields were obtained in repeated experiments:

Fraction A from the unsaponifiable fraction: 20 to 25% by weight

Unsaponifiable fraction from the dry raw material: 0.7 to 1% by weight

Preparation of the Supercritical-$CO_2$-Extract Used in the Experiments ("SCExtract")

5 kg of dry pulp of the fruit of the plant *Argania spinosa* (the moisture content was 19.2%) ("raw material") was extracted using a supercritical fluid. The raw material was placed in a vessel in the presence of an extraction fluid in a supercritical state (carbon dioxide and 8% by weight of ethanol as co-solvent). The pressure applied was 280 bar, the temperature 45° C., the flow rate of the supercritical fluid 25 kg/h. 123 kg of supercritical fluid were necessary to extract 210 g of raw material.

Active compounds of this extract are triterpenes (lupeol, erythrodiol, alpha amyrine, beta amyrine) esterified with one or several fatty acids.

Example 1

Toxicity Tests and Growth Tests on Human Fibroblasts

The purpose of these tests was to evaluate the toxicity and then the regenerating and revitalising activities on human fibroblasts cultured in vitro.

Human fibroblasts were inoculated in a standard medium of cell culture with foetal calf serum (FCS). After an incubation of 1 day at 37° C. and $CO_2$=5% (the atmosphere used was air with 5 Vol.-% carbon dioxide), the growth medium was exchanged for a standard medium with a range of concentrations for each ingredient to be tested. After an incubation of 3 days, the number of viable cells was determined by evaluation of the levels of cellular proteins (Bradford's method) Cell protein concentration was determined according to Bradford (Bradford M. M. A rapid and sensitive method for the quantification of microgram quantities of protein utilizing the principle of protein-dye binding. Anal. Biochem. (1977) vol 72, pages 248-254).

The triterpene fraction was compared to erythrodiol. The results in the following table are expressed in % against control (cell culture medium without ingredient).

|  | unsaponifiable extract prepared from the hexane-extract as described | triterpene fraction | erythrodiol |
| --- | --- | --- | --- |
| Control | 100% | 100% | 100% |
| 0.0001% | 108% | 112% | 104% |
| 0.0003% | 115% | 124% | 105% |
| 0.001% | 142% | 143% | 43% |
| 0.003% | 118% | 31% | 34% |
| LD50 (% w/v) | 0.009% | 0.003% | 0.0009% |

"w/v" means "weight by volume" (1% w/v means 1 g per 100 ml).

These experiments show that the triterpene fraction is safe at concentrations up to 0.001% while erythrodiol is safe at concentrations up to 0.0003% in the cell culture tested. The triterpene fraction at a concentration of 0.001% has distinctly improved the cell growth of human fibroblasts.

Furthermore these experiments show that the unsaponifiable extract has distinctly stimulated the growth of fibroblasts.

Example 2

Survival Efficacy Test on Human Fibroblasts

The purpose of this test was to evaluate the toxicity and then the regenerating and revitalising activities on human fibroblasts cultured in vitro.

Human fibroblasts were inoculated in a standard medium of a cell culture with foetal calf serum (FCS). After an incubation of 3 days the cells became quiescent, then the growth medium was exchanged for a standard medium with a range of concentrations for each ingredient to be tested. After an incubation of 3 days, the number of viable cells was determined by evaluation of the levels of and the rates of cellular DNA (fluorescent probe), ATP (enzymatic method), proteins (Bradford's method) and GSH which is evaluated according to the method of Hissin (Hissin P. J., Hilf R. A, fluorometric method for determination of oxidised and reduced Glutathione in tissues. Analytical Biochemistry (1977) volume 74, pages 214-226).

ATP (or adenosine triphosphate) is a compound rich in energy. It is mainly produced by mitochondria. The cells need ATP for the activity of many enzymes which control the cytoskeleton, the ionic channels, the nutriment intake, and a lot of other biological processes.

Glutathione (GSH) is a peptide produced by cells to protect them from oxidative stress or certain pollutants like Mercury or Lead. The three amino acids involved in the reduced form of GSH are linked by specific cytoplasmic enzymes, which use ATP. An increase in the GSH level enhances the activity of glutathion-5-transferase, a detoxification enzyme.

The following table shows the results of the tests.

|  | Dose (% w/v) | DNA | ATP | Proteins | GSH/proteins |
| --- | --- | --- | --- | --- | --- |
| control | 0 | 100% | 100% | 100% | 100% |
| triterpene fraction | 0.0003% | 109% | 118% | 127% | 151% |
|  | 0.001% | 130% | 141% | 162% | 131% |
|  | 0.003% | 63% | 43% | 59% | 115% |
| erythrodiol | 0.00001% | 96% | 107% | 100% | 120% |
|  | 0.00003% | 108% | 99% | 97% | 141% |
|  | 0.0001% | 78% | 66% | 91% | 101% |
|  | 0.0003% | 59% | 73% | 83% | 88% |
| SC-extract | 0.001% | 109% | 124% | 115% | 104% |
|  | 0.003% | 120% | 138% | 122% | 135% |
|  | 0.01% | 136% | 162% | 127% | 215% |

In the last column of this table "GSH/proteins" is used, because the increase of GSH is expressed in relation to the increase in proteins in general.

The triterpene fraction at a concentration of 0.001% has distinctly enhanced the amount of DNA, ATP and proteins. Compared to that erythrodiol has modified the amount of GSH synthesized by human fibroblasts cultured in vitro only at a concentration of 0.00003%.

The SC-extract has distinctly stimulated the cell metabolism of human fibroblasts cultured in vitro.

Example 3

Cytophotoprotection of Human Fibroblasts Against UV-A Radiation

The cytoprotection against UV-A radiation was evaluated by a test on human fibroblasts because UV-A radiation penetrates through the epidermis until the derma where it induces oxidative stress (DALLE CARBONARE M, PATHAK M A; Skin photosensitising agents and the role of reactive oxygen species in photoaging; JOURNAL OF PHOTOCHEMISTRY & PHOTOBIOLOGY, 1992, 14, 1-2, pages 105-124. This oxidative stress was evaluated in vitro by measuring of the level of released MDA (malonaldehyde) and of intracellular GSH (reduced glutathione) (Morliere P., Moisan A., Santus R., Huppe G., Mazière J. C., Dubertret L.: UV-A induced lipid peroxydation in cultured human fibroblasts. Biochim. Biophys. Acta, 1084, 3, pages 261-269 (1991)).

Expressed in keywords, the experiments were carried out as follows:
Inoculation of human fibroblasts within a growth medium (standard medium with foetal calf serum (FCS)
Incubation 3 days at 37° C., $CO_2$=5%
Exchange of growth medium with balanced salt solution
Irradiation of fibroblasts by UV-A: 20 J/cm² (black light TFWN lamp) (A TFWN lamp is a certain type of marketed sunlamp well known to the skilled artisan)
Exchange of growth medium with standard medium without FCS but containing ingredient to be tested
Incubation 3 days at 37° C., $CO_2$=5%
Recovery of supernatant medium for spectrophotometric determination of the malonaldialdehde (or MDA) rate
Cells number determined by evaluation of the levels of cellular proteins (Bradford's method) and the rate of cellular GSH was evaluated according to the method of Hissin The following table summarizes the results in % against control

| Name: | dose | Released MDA | cell's protein | GSH/protein |
|---|---|---|---|---|
| Control without UV | / | 0% | 100% | 100% |
| UV-A 20 Jcm² | / | 100% | 115% | 70% |
| UV-A + Tocopherol | 0.0003% | 23% | 106% | 89% |
| UVA + triterpene fraction | 0.0003% | 79% | 161% | 69% |
| | 0.001% | 51% | 150% | 92% |
| UVA + erythrodiol | 0.0001% | 81% | 139% | 94% |
| | 0.0003% | 70% | 42% | 22% |

The results of the experiments can be interpreted and summarized as follows:
The UVA irradiation has induced a strong increase of the level of released MDA and a decrease of around 30% of the level of intracellular GSH.
Tocopherol has strongly protected the human fibroblasts from toxic UVA effects.
The triterpene fraction at a concentration of 0.001% has distinctly protected the human fibroblasts from toxic UV-A effects but this effect could be mediated by a stimulation of GSH synthesis.
Erythrodiol has moderately protected the human fibroblasts from toxic UV-A effects and this effect could be mediated by a stimulation of GSH synthesis Example 4

Cytophotoprotection of Human Keratinocytes Against UV-B Radiation

The purpose of these experiments was to demonstrate the cytophotoprotection of human keratinocytes against UV-B radiation.

UV-B irradiation (from 280 to 320 nm) of the human skin induces a cutaneous inflammation mainly by activation of an enzyme (phospholipase A2 or PLA2), which releases arachidonic acid from the cell membranes of the cells of the skin (V. A. De Leo, D. Hanson, I. B. Weinstein and L. C. Harber—Ultraviolet radiation stimulates the release of arachidonic acid from mammalian cells in culture—Photochemistry and Photobiology (1985) volume 41N°1 pages 51-56). Then other specific enzymes (so called cyclo-oxygenases) transform arachidonic acid in active components called prostaglandines (or PG) which are secreted out of the cells. The fixation of certain prostaglandins (PGE2) on specific skin receptors is followed by redness and swelling as after a sunburn. On cultured human cells, these UV-B effects on cell membranes are associated with a release in the supernatant medium of a cytoplasmic enzyme, the Lactate Dehydrogenase or LDH (B. Bonnekoh, B. Farkas, J. Geisel and G. Mahrle—Lactate dehydrogenase release as an indicator of dithranol-induced membrane injury in cultured human keratinocytes. Dermatological research (1990) volume 282, pages 325-331).

Expressed in keywords, the experiments were carried out as follows:
Inoculation of human keratinocytes within growth medium (standard medium with fetal calf serum (FCS)
Incubation 3 days at 37° C., $CO_2$=5%
Exchange of growth medium with balanced salt solution containing ingredient to be tested
Irradiation of keratinocytes by UV-B: 50 mJ/cm² (DUKE GL40E lamp) (A DUKE GL40E lamp is a certain type of marketed sunlamp well known to the skilled artisan)
Incubation 1 day at 37° C., $CO_2$=5%
Numeration of adherent cells after trypsination (trypsination is a process based on the use of the enzyme trypsine which is a protease allowing the retrieval of cell from the support in order to seed the cells into a bigger flask and therefore to expand the cell culture)
Recovery of supernatant medium for spectrophotometric determination of the activity of LDH, and PGE2 by ELISA method The following table summarizes the results for mono-layers of human keratinocytes in % against control.

| Name: | dose | Cell number | Released LDH | Released PGE2 |
|---|---|---|---|---|
| Control (not irradiated) | / | 100% | 0% | 0% |
| Control/UVB (30 mJ/cm²) | / | 26% | 100% | 100% |

-continued

| Name: | dose | Cell number | Released LDH | Released PGE2 |
|---|---|---|---|---|
| UVB + Aspirin | 0.0003% | 67% | 13% | 0% |
| UVB + Indomethacine | | 34% | 77% | 0% |
| UVB + TRITERPEN FRACTION | 0.001% | 35% | 61% | 67% |
| | 0.003% | 44% | 40% | 52% |
| UVB + erythrodiol | 0.00001% | 21% | 135% | 135% |
| | 0.00003% | 23% | 118% | 164% |

The results of the experiments can be interpreted and summarized as follows:

The UVB irradiation has induced a strong increase of the level of released LDH and a decrease of 74% of the cell's number.

Aspirin has distinctly reduced the UV toxic effects on the number of viable cells (cell number and released LDH) and on the release of inflammatory mediators such as PGE2.

Indomethacin has moderately reduced the UV toxic effects on the number of viable cells (cell number and released LDH) but the release of inflammatory mediators such as PGE2 was drastically reduced.

The triterpene fraction at a concentration of 0.003% has distinctly reduced the UV-induced toxic effects on the rate of viable cells (cell number and released LDH) and the release of inflammatory mediators such as PGE2 was drastically reduced.

Erythrodiol has not modified the UV toxic effects on the cultured human keratinocytes.

Example 5

Inhibition Effect on Proteases

Background:

During inflammatory processes, skin proteases like elastase are secreted from polymorphonuclear neutrophilic granulocytes and from macrophages. These proteases catalyse the fragmentation of very important macromolecules of the skin such as proteoglycans and elastin.

Example 5a

Elastine—Congo Red as Natural Substrate

This test was carried out with an elastase from pancreas on Elastin labelled with Congo red. The time of incubation was 30 minutes at room temperature and the optical density of released Congo red was recorded after centrifugation at a wavelength of 520 nm. al-antitrypsine was used as positive reference.

The following table summarizes the results expressed as EC 50 in % w/v. (EC 50 in % w/v is the concentration in % w/v which reduces the enzymatic activity by 50%.)

| Name: | Elastase |
|---|---|
| A1 anti trypsine | 0.03% |
| erythrodiol | 0.08% |

These results demonstrate that erythrodiol shows a good potential to inhibit the activity from proteases such as elastase.

The invention claimed is:

1. A method of revitalizing skin, stimulating skin metabolism or protecting skin from UV-A and UV-B radiation, comprising applying to skin in need thereof a composition comprising:
   (a) an extract from the pulp of *Argania spinosa* fruit selected from the group consisting of
      (i) a lipophilic supercritical $CO_2$ extract comprising triterpenes esterified with fatty acids and
      (ii) an unsaponifiable triterpene fraction consisting essentially of lupeol, α-amyrine, β-amyrine, taraxasterol and psi-taraxasterol; and
   (b) at least one dermopharmaceutical or cosmetic auxiliary and/or additive.

2. The method according to claim 1, wherein the total amount of extract present in the composition is 0.01-25% by weight, based on dry weight.

3. The method according to claim 1, wherein the total amount of extract present in the composition is 0.03-5% by weight, based on dry weight.

4. The method according to claim 1, wherein the total amount of extract present in the composition is 0.03-0.6% by weight, based on dry weight.

5. The method according to claim 2, wherein the total amount of auxiliaries and additives is 1-50% by weight.

6. The method of claim 1, wherein said extract (a)(ii) comprises a fraction of a hexane extract.

7. A composition comprising
a lipophilic supercritical $CO_2$ extract from the pulp *Argania spinosa* fruit, the extract comprising triterpenes esterified with fatty acids
and
at least one dermopharmaceutical or cosmetic auxiliary and/or additive.

8. The composition of claim 7, wherein the total amount of extract present in the composition is 0.01-25% by weight, based on dry weight.

9. The composition of claim 8, wherein the total amount of extract present in the composition is 0.03-5% by weight, based on dry weight.

10. The composition of claim 9, wherein the total amount of extract present in the composition is 0.03-0.6% by weight, based on dry weight.

11. The composition of claim 7, wherein the total amount of auxiliaries and additives is 1-50% by weight.

12. A lipophilic supercritical $CO_2$ extract from the pulp of *Argania spinosa* fruit comprising triterpenes esterified with fatty acids.

* * * * *